United States Patent [19]
Drinon et al.

[11] Patent Number: 5,396,800
[45] Date of Patent: Mar. 14, 1995

[54] APPARATUS AND METHOD FOR INSPECTING A CONTROL ROD DRIVE MECHANISM PENETRATION TUBE FOR DEGRADATION

[75] Inventors: David S. Drinon, Oakmont; Mustan Attaar; Warren R. Junker, both of Monroeville; Robert E. Shannon, Export, all of Pa.

[73] Assignee: Westinghouse Electric Corporation, Pittsburgh, Pa.

[21] Appl. No.: 32,083

[22] Filed: Mar. 17, 1993

[51] Int. Cl.⁶ ............... G01N 29/06; G01N 29/10
[52] U.S. Cl. .................. 73/623; 376/249; 376/252; 324/221
[58] Field of Search ............ 73/620, 622, 623, 627, 73/633, 644; 376/245, 249, 252; 324/219, 220, 221, 226

[56] References Cited

U.S. PATENT DOCUMENTS

| | | | |
|---|---|---|---|
| 3,584,504 | 6/1971 | Proctor et al. | 73/623 |
| 4,855,677 | 8/1989 | Clark, Jr. et al. | 324/220 |
| 4,856,337 | 8/1989 | Metala et al. | 73/623 |
| 4,889,679 | 12/1989 | Snyder et al. | 376/258 |
| 4,901,578 | 2/1990 | Brill, III | 73/623 |
| 5,267,481 | 12/1993 | Smith | 73/623 |

Primary Examiner—Hezron E. Williams
Assistant Examiner—Rose M. Finley
Attorney, Agent, or Firm—Walter S. Stevens

[57] ABSTRACT

Apparatus and method for inspecting a tubular member for degradation, which tubular member may be a control rod drive mechanism (CRDM) penetration tube of the kind typically found in nuclear power reactor pressure vessels. The CRDM penetration tube includes a thermal sleeve concentrically disposed therein, the sleeve being radially rotatable and axially translatable within the tube. However, the sleeve may be nonhomogeneous, which nonhomogeneity could undesirably mask the inspection signal as the inspection sensor is radially and axially moved in order to inspect the tube. The apparatus includes a support body sized to be disposed in the sleeve, an expandable bladder connected to the support body to engage the sleeve for securing the support body to the sleeve, one or more sensors connected to the support body for sensing the degradation in the tube, and a rotator connected to the support body for simultaneously rotating the support body, the bladder, the sensor and the sleeve in the tube to radially scan the tube. A pusher/puller mechanism is also provided, the pusher/pusher mechanism being connected to the support body for simultaneously translating the support body, the bladder, the sensor and the sleeve to axially scan the tube. As the support body is rotated and translated, the sleeve is stationary with respect to the sensor because the bladder secures the sleeve to the support body; thus, as the support body, and the sensor connected thereto are rotated and translated, the sleeve will be rotated and translated to a like extent. In this manner the material properties of the sleeve are radially and axially invariant relative to the sensor, for obtaining a more precise inspection of the tube.

29 Claims, 7 Drawing Sheets

APPARATUS AND METHOD FOR INSPECTING A CONTROL ROD DRIVE MECHANISM PENETRATION TUBE FOR DEGRADATION

BACKGROUND

This invention generally relates to inspection apparatus and methods and more particularly relates to an apparatus and method for inspecting a tubular member for degradation, which tubular member may be a control rod drive mechanism penetration tube of the kind typically found in nuclear power reactor pressure vessels.

Although devices and methods for inspecting tubular members are known in the prior art, it has been observed that prior art devices and methods have certain operational problems associated with them which make these devices and methods unsuitable for inspecting control rod drive mechanism penetration tubes of the kind typically found in nuclear power reactor pressure vessels. However, before these problems can be appreciated, some background is necessary as to the structure and operation of a typical nuclear power reactor and its associated control rod drive mechanism penetration tubes.

In this regard, a nuclear power reactor is a device for producing heat by controlled fission of fissionable material contained in fuel assemblies. A plurality of the fuel assemblies are grouped in a sealed reactor pressure vessel to define a nuclear reactor core therein. Pressurized liquid moderator coolant (i.e., borated demineralized water) is caused to circulate through the pressure vessel and over the fuel assemblies for assisting in the fission process and for removing the heat produced by fission of the fissionable material contained in the fuel assemblies.

However, the fission process in the reactor core must be suitably controlled for safety reasons. Therefore, a plurality of vertically movable control rods are each connected to respective ones of a plurality of control rod drive mechanisms (CRDMs) which are connected to the top of the reactor pressure vessel by means of a CRDM penetration tube that penetrates the pressure vessel. Each CRDM vertically positions its respective control rods within the fuel assemblies associated therewith to adjust reactor core reactivity so that the fission process is suitably controlled. The moving internal components of each CRDM, which moves its respective control rods connected thereto, extend through a thermal sleeve mounted in and surrounded by the CRDM penetration tube. The sleeve is freely rotatable and axially movable within the penetration tube. The purpose of the thermal sleeve is to provide a measure of thermal insulation for the penetration tube. The penetration tube itself is welded to the pressure vessel.

Applicants have discovered that, due to degradation of the wall of the penetration tube, through-wall cracks may occur in the tube sufficient to cause leaks of the borated coolant from the reactor pressure vessel. Such a tube leak ultimately may lead to undesirable reactivity anomalies in the reactor core because the inventory of the borated moderator coolant used to assist the fission process is momentarily reduced by the leak. In addition, because the tube forms a portion of the reactor pressure boundary, any such leak may affect the pressure and thus the temperature of the moderator coolant. Variation in the coolant temperature also undesirably affects core reactivity. Such reactivity anomalies are undesirable for safety reasons. It is therefore prudent to inspect the CRDM penetration tubes for any degradation or cracks that might lead to leakage of the coolant. Such an inspection may be attempted by means of an eddy current inspection device that emits electromagnetic energy, or by an ultrasonic inspection device that emits sonic energy, propagating into the penetration tube to detect any degradation in the tube. Such an inspection device is preferably capable of radially and axially inspecting the tube by moving both radially and axially to scan the tube for degradation.

In typical prior art methods of tube inspection, an inspection device is centrally disposed in a tube and then merely moved radially and axially to scan the tube for degradation. However, applicants have discovered that in the case of CRDM penetration tubes, the thermal sleeve, which is concentrically mounted in the CRDM penetration tube, presents a barrier to suitable inspection of the penetration tube. This is so because, in the case of CRDM penetration tubes, centrally disposing the inspection device in the penetration tube also necessarily requires that it be centrally disposed within the sleeve, because the sleeve is concentrically mounted within the penetration tube. Therefore, the sleeve is interposed between the inspection device and the penetration tube and thus presents a barrier to suitable inspection of the tube. This barrier undesirably interferes with the electromagnetic or sonic energy radially emitted and received by the inspection device. This interference is caused by the nonuniform material properties of the sleeve. That is, the "as-built" thermal sleeve may posses nonhomogeneous or nonuniform material properties that vary from nominal design values. Such nonuniform material properties is evinced by radially and axially varying electromagnetic and sonic properties caused by radially and axially varying sleeve density even though the sleeve is nominally formed of a single material (e.g., "INCONEL ALLOY 600"). Moreover, such a sleeve may have radially and axially varying dimensions that differ from nominal values due to variations in the manufacturing process used to make the sleeve. For example, axial portions of such a sleeve may have an oval transverse cross section rather than a perfectly round transverse cross section. Such nonuniform material properties and dimensions interfere with the inspection sensor signals received during the inspection process because the presence of the flaw detected by the inspection device will be undesirably masked by the volumetrically-varying (i.e., nonuniform or nonhomogeneous) material properties of the intervening sleeve. Therefore, a problem in the art is to inspect such a penetration tube, even in the presence of an intervening sleeve having nonuniform material properties and dimensions.

Apparatus and methods for inspecting tubular members for degradation are known. One such apparatus is disclosed in commonly owned U.S. Pat. No. 4,856,337 titled "Apparatus and Method For Providing A Combined Ultrasonic And Eddy Current Inspection Of A Tube" issued Aug. 15, 1989 in the name of Michael J. Metala, et al. Although this patent discloses an inspection device for inspection of a tube, this patent does not appear to disclose an apparatus and method for suitably inspecting a control rod drive mechanism penetration tube of the kind typically-found in nuclear power reactor pressure vessels.

Therefore, what is needed is an apparatus and method for inspecting a tubular member for degradation, which tubular member may be a control rod drive mechanism penetration tube of the kind typically found in nuclear power reactor pressure vessels.

SUMMARY

Disclosed herein are an apparatus and method for inspecting a tubular member for degradation, which tubular member may be a control rod drive mechanism (CRDM) penetration tube of the kind typically found in nuclear power reactor pressure vessels. The CRDM penetration tube includes a thermal sleeve concentrically disposed therein, the sleeve being radially rotatable and axially movable within the tube. Due to deviations from nominal design values, the tube may be nonhomogeneous, which nonhomogeneity could undesirably mask the inspection signal as the inspection sensor is radially and axially moved in the sleeve to order to inspect its surrounding tube. The apparatus of the invention includes a support body sized to be disposed in the sleeve, an expandable bladder connected to the support body to engage the sleeve for securing the support body to the sleeve, at least one sensor connected to the support body for sensing the degradation in the tube, and a rotator connected to the support body for rotating the support body, the sensor and the sleeve in order to radially scan the tube. A pusher/puller mechanism is also provided, the pusher/pusher mechanism being connected to the support body for translating the support body, the sensor and the sleeve in order to axially scan the tube for degradation. As the support body is rotated and translated, the sleeve is stationary with respect to the sensor because the bladder secures the sleeve to the support body; thus, as the support body, and the sensor connected thereto, is rotated and translated, the sleeve will be rotated and translated to a like extent. In this manner the material properties of the sleeve are invariant relative to the sensor, thereby allowing-for a more precise inspection.

In its broad form, the invention is an apparatus for inspecting a tubular member for degradation, the tubular member surrounding a rotatable sleeve, comprising a support body adapted to be disposed in the sleeve; securing means connected to said support body and adapted to engage the sleeve for securing said support body to the sleeve; sensor means connected to said support body for sensing the degradation in the tubular member; and rotation means connected to said support body for rotating said support body, whereby said support body, said securing means, said sensor means and the sleeve simultaneously rotate in the tubular member as said rotation means rotates said support body.

In its broad form, the invention is also a method of inspecting a tubular member for degradation, the tubular member surrounding a rotatable sleeve, comprising the steps of disposing a support body in the sleeve, the support body having a bladder and a sensor connected thereto; securing the support body to the sleeve by engaging the bladder with the sleeve; operating the sensor for sensing the degradation in the tubular member; rotating the support body by operating a rotator connected thereto, whereby the support body, the bladder, the sensor and the sleeve simultaneously rotate in the tubular member as the rotator rotates the support body.

An object of the present invention is to provide an apparatus and method for inspecting a tubular member for degradation, which tubular member may be a control rod drive mechanism penetration tube of the kind typically found in nuclear power reactor pressure vessels.

Another object of the present invention is to provide an apparatus and method for inspecting a CRDM penetration tube for degradation, even in the presence of an intervening sleeve having nonuniform material properties and dimensions.

A feature of the present invention is the provision of a support body adapted to be disposed in a freely rotatable and axially movable CRDM thermal sleeve, an expandable bladder connected to the support body to engage the sleeve for securing the support body to the sleeve, a sensor connected to the support body for sensing the degradation in the tube, and a rotator connected to the support body for rotating the support body, the sensor and the sleeve to radially scan the tube for degradation.

Another feature of the present invention is the provision of a pusher/puller mechanism connected to the support body for translating the support body, the sensor and the sleeve to axially scan the tube for degradation.

An advantage of the present invention is that the material properties of the sleeve are invariant relative to the sensor as the support body, the sensor and the sleeve are rotated and translated because the sleeve is stationary with respect to the sensor.

These and other objects, features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings wherein:

DESCRIPTION OF THE PREFERRED EMBODIMENT(S)

Disclosed hereinbelow are an apparatus and a method for inspecting a tubular member for degradation, which tubular member may be a control rod drive mechanism (CRDM) penetration tube of the kind typically found in nuclear power reactor pressure vessels. It known that due to degradation of the penetration tube wall, cracks may occur in the tube wall sufficient to allow leaking of the borated coolant through the tube wall, which leaking ultimately may lead to undesirable reactivity anomalies in the nuclear reactor core. Such cracks may, for example, be caused by stress and corrosion due to the acidic effect of the borated coolant and the relatively high temperature and pressure of the coolant. It is therefore prudent to inspect CRDM penetration tubes for any degradation or cracks that might lead to leakage of the coolant. However, a thermal sleeve, which may have nonuniform material properties, is mounted in and surrounded by the CRDM penetration tube. The nonuniformity of the thermal sleeve interferes with the inspection process because the presence of the penetration tube flaw detected by the inspection device will be undesirably masked by the nonuniform (i.e., volumetrically-varying) material properties of the intervening sleeve. Therefore, a problem in the art is to inspect the penetration tube, even in the presence of an intervening nonuniform sleeve. According to the invention, this problem is solved by providing a suitable apparatus and method for inspecting the penetration tube for degradation, even in the presence of the-intervening nonuniform sleeve.

However, before describing the subject matter of the present invention, it is instructive first to briefly describe the structure and operation of a typical nuclear power reactor and its associated control rod drive mechanism penetration tubes.

Figure 1:
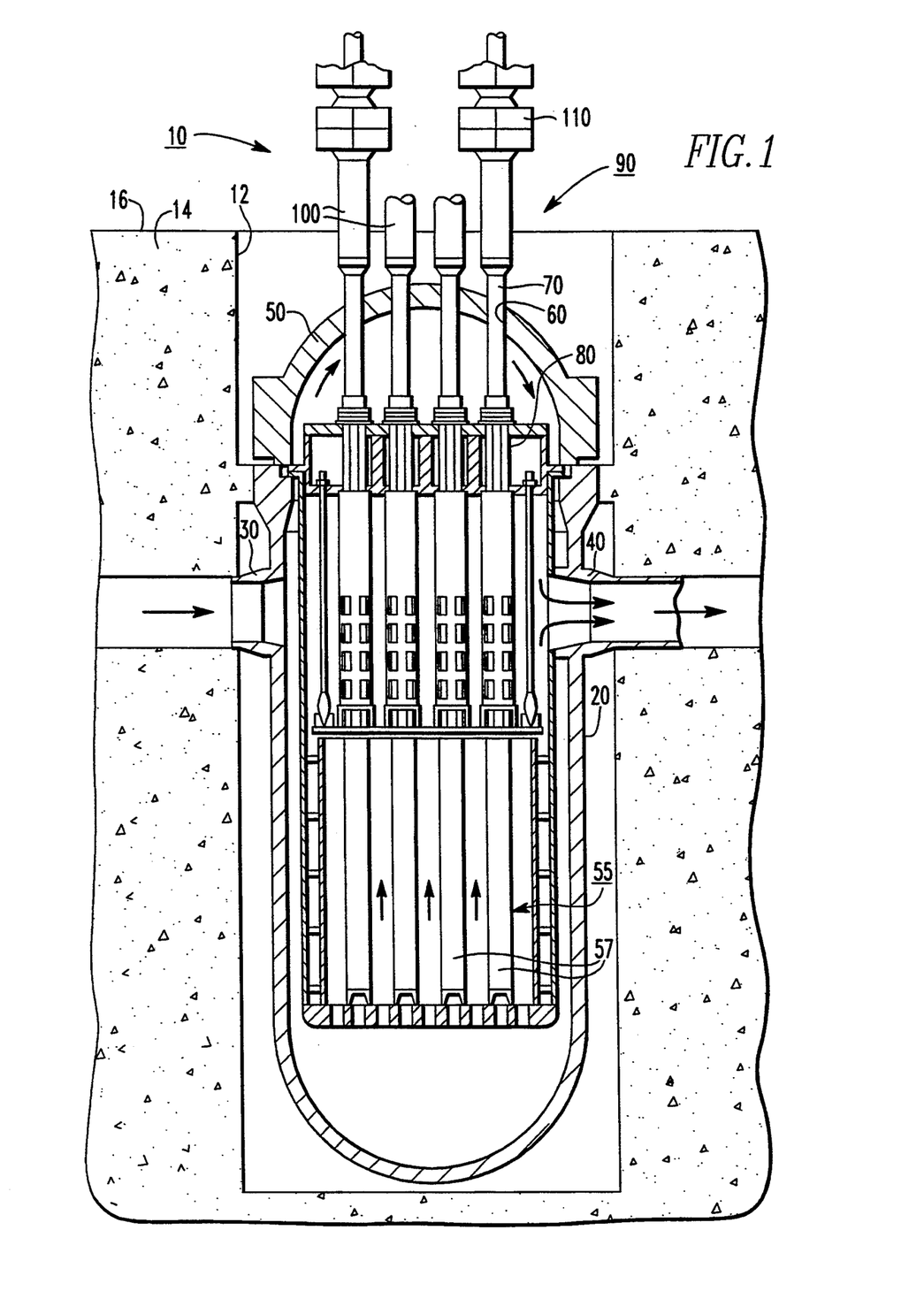
FIG. 1 shows in partial vertical section, a typical nuclear power reactor pressure vessel with parts removed for clarity, the pressure vessel being disposed in a reactor cavity and having a closure head penetrated by a plurality of Control Rod Drive Mechanism (CRDM) penetration tubes.
Figure 2:
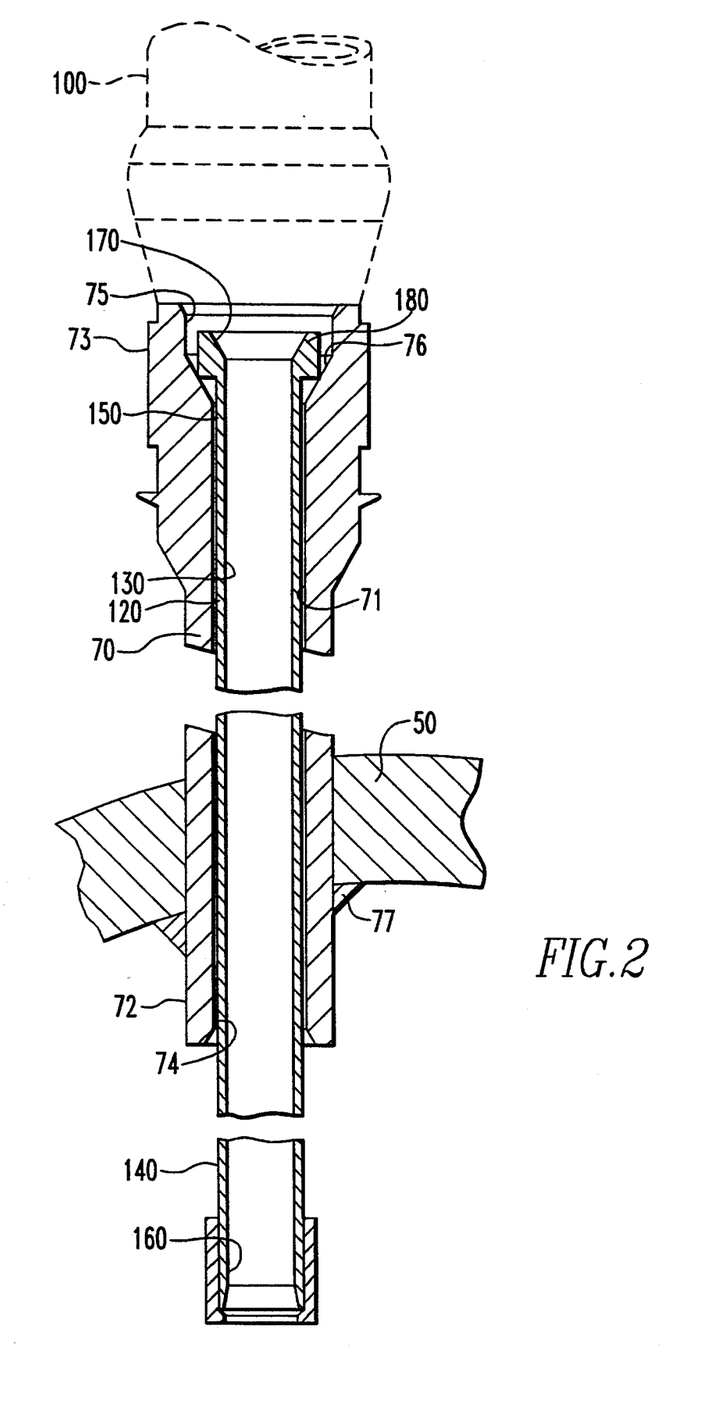
FIG. 2 shows-in vertical section one of the penetration tubes.

Therefore, referring to FIGS. 1 and 2, there is shown a typical nuclear power reactor, generally referred to as 10, for producing heat by controlled fission of fissionable material (not shown). Reactor 10 is disposed in a reactor cavity 12 defined by a containment structure 14 having a top surface 16 thereon. Reactor 10 includes a reactor pressure vessel shell 20 open at its top end and having a plurality of inlet nozzles 30 and outlet nozzles 40 attached to the upper portion thereof (only one of each nozzle is shown). A hemispherical reactor vessel closure head 50, which may be carbon steel, is mounted atop vessel shell 20 and is sealingly attached to the open top end of vessel shell 20 so that closure head 50 sealingly caps vessel shell 20. Capping vessel shell 20 in this manner allows for suitable pressurization of the coolant (not shown) circulating through vessel shell 20 as reactor 10 operates. The coolant may be borated demineralized water maintained at a relatively high pressure of approximately 2500 psia and a temperature of approximately 650 degrees Fahrenheit.

Still referring to FIGS. 1 and 2, disposed in reactor 10 is a nuclear reactor core, generally referred to as 55, comprising a plurality of nuclear fuel assemblies 57 containing the fissionable material. Formed through the top of closure head 50 are a plurality of closure head openings 60 for receiving respective ones of a plurality of generally tubular control rod drive mechanism (CRDM) penetration tubes 70, each penetration tube 70 having an inner diameter 71. Each penetration tube 70 is affixed to closure head 50 by weldments 77. Penetration tube 70 may be made from corrosion resistant "INCONEL ALLOY 600" which comprises by weight percent approximately 76.0% nickel, 0.08% carbon, 0.5% magnesium, 8.0% iron, 0.008% sulfur, 0.25% copper, and 15.5% chromium. Penetration tube 70 has a proximal end portion 72 and a distal end portion 73 defining an open first mouth 74 and an open second mouth 75, respectively. Open second mouth 75 itself forms an annular chamfered land 76, for reasons provided hereinbelow. As used herein, the terminology "proximal end portion" means that end portion hearer reactor core 55 and the terminology "distal end portion" means that portion further away from reactor core 55. Moreover, each CRDM penetration tube 70 houses a control rod drive shaft (not shown) extending therethrough, the drive shaft engaging at least one movable control rod cluster (not shown) comprising absorber or poison material for controlling the fission process in reactor core 55.

Referring again to FIGS. 1 and 2, connected to penetration tube 70 is a CRDM, generally referred to as 90, for axially moving drive rod 80 and thus the control rod cluster connected thereto. CRDM 90 comprises a generally tubular pressure housing 100, which may be "TYPE 304" stainless steel which comprises by weight percent approximately 0.08% carbon, 20% chromium, 11% nickel, and 78.92% iron. Attached to pressure housing 100 is an electromagnetic coil stack assembly 110 for electromagnetically axially moving drive rod 80 as coil stack assembly 110 is electrically energized.

As reactor 10 operates, the coolant enters shell 20 and circulates therethrough generally in the direction of the arrows shown in FIG. 1. As the coolant circulates through shell 20, it also circulates over fuel assemblies 57 for assisting in the fission process and for removing the heat produced by fission of the fissionable material contained in fuel assemblies 57. Coil stack assemblies 110 axially move the control rod clusters in and out of fuel assemblies 57 to suitably control the fission process therein. The heat generated by fuel assemblies 57 is ultimately transferred to a turbine-generator for producing electricity in a manner well known in the art of nuclear powered electricity production.

As best seen in FIG. 2, inner diameter 71 of penetration tube 70 surrounds a generally tubular thermal sleeve 120 concentrically mounted in tube 70, for reasons provided presently. Sleeve 120 has an inside diameter 130. Sleeve 120 also has a proximal end portion 140 and a distal end portion 150 defining an open first mouth 160 and an open second mouth 170, respectively. Distal end portion 150 of sleeve has an annular flange 180 surrounding open second mouth 170 for mounting sleeve 120 on chamfered land 76 of tube 70. Flange 180 is mounted on land 76 so that sleeve 120 is freely suspended therefrom in inner diameter 71 of tube 70. It will be appreciated from the description hereinabove that flange 180 is not affixed to land 76; rather, flange 180 merely rests on land 76 and is therefore circularly slidable on land 76. Thus, sleeve 120 is freely rotatable and axially movable (i.e., translatable) in inner diameter 71 because sleeve 120 is freely rotatably slidable on land 76 and freely axially suspended in inner diameter 71.

Still referring to FIG. 2, sleeve 120 may not be homogeneous. Thus, sleeve 120 may have nonuniform material properties. That is, sleeve 120 may possess nonhomogeneous or nonuniform material properties that vary from nominal design values. Such nonuniform material properties may be evinced by radially and axially varying electromagnetic and sonic properties caused by radially and axially varying density even though the sleeve 120 is formed of a single material (i.e., "INCONEL ALLOY 600"). Moreover, such a sleeve 120 may have radially and axially varying dimensions that differ from nominal values due to variations in the manufacturing process used to make sleeve 120. Such nonuniform material properties interfere with inspecting tube 70 for degradation (not shown) because the presence of the flaw detected will be undesirably masked by the volumetrically-varying (i.e., nonhomogeneous) material properties of sleeve 120. However, it is nonetheless desirable to inspect CRDM penetration tube 70 for degradation, even in the presence of intervening sleeve 120, which may have nonuniform material properties and dimensions.

Turning now to FIGS. 3, 4, 5, 6, 7, 8 and 9, there is shown the subject matter of the present invention, which is an apparatus, generally referred to as 190, for inspecting a tubular member for degradation, which tubular member may be control rod drive mechanism penetration tube 70 of the kind typically found in nuclear power reactor pressure vessels 10. Apparatus 190 comprises an elongate generally cylindrical support body 200 sized to be disposed in inside diameter 130 of sleeve 120 and moved along the longitudinal axis of sleeve 120. Support body 200 has an exterior surface 210 thereon and a channel 220 therethrough terminating in an opening 230 on exterior surface 210 for reasons provided hereinbelow. Surrounding a portion of support body 200 and sealingly connected thereto is securing means, such as a flexible radially expandable and contractible bladder 240, adapted to intimately engage inside diameter 130 of sleeve 120 for securing support body 200 to inside diameter 130. Bladder 240 defines a variable volume 245 therein capable of receiving a fluid, such as water, for pressurizing bladder 240 to radially expand it into intimate engagement with inside diameter 130 of sleeve 120. Moreover, bladder 240 covers opening 230. In the preferred embodiment, bladder 240 may be "PELLETHANE CPR-2103-55D" available from The UpJohn Company, CPR Division, located in Torrance, Calif.

Still referring to FIGS. 3, 4, 5, 6, 7, 8 and 9, connected to support body 200 is sensor means, such as a first eddy current sensor 250, for sensing degradation in penetration tube 70. In the preferred embodiment of the invention, there also may be a second eddy current sensor 260 connected to support body 200 for sensing degradation in penetration tube 70. First sensor 250 is capable of sensing axially-oriented degradation and second sensor 260 is capable of sensing circumferentially-oriented degradation in tube 70. Sensors 250/260 are each adapted radially transmit electromagnetic energy penetrating sleeve 120 and tube 70 to generate electromagnetic eddy current perturbations (not shown) therein. Sensors 250/260 are also adapted to receive or sense the eddy currents generated in sleeve 120 and tube 70. As well known in the art, the shape and intensity of eddy currents generated in sleeve 120 and tube 70 are a function of the continuity of the material comprising sleeve 120 and tube 70. Thus, changes in the generated eddy currents are affected by any discontinuities (e.g., degradation) present in the material. Sensors 250/260 sense these changes to detect such discontinuities.

Referring again to FIGS. 3, 4, 5, 6, 7, 8 and 9, each sensor 250/260 comprises a housing 270a/270b, respectively, connected to support body 200. In addition, attached to housing 270b of sensor 260, and thus indirectly connected to support body 200, may be centering means, such as a disk-shaped centering device 275, for centering support body 200 (in addition to sensors 250/260 and bladder 240 connected thereto) in inner diameter 71. Each housing 270a/270b may have a hole 280a/280b, respectively, therethrough for allowing the unimpeded transmission and sensing of the electromagnetic energy. Housed in housing 270a and connected to support body 200, such as by a support 285, is an axial-transmission coil, referred to herein as axial coil 290, for transmitting electromagnetic flux to intercept axially-oriented degradation (not shown) in tube 70. Axial coil 290 may be generally semi-annular in transverse cross section and has a longitudinal axis oriented generally perpendicularly with respect to the longitudinal axis of tube 70. Moreover, housed in housing 270b and connected to support body 200, such as by a support 295, is a circumferential-transmission coil, referred to herein as circumferential coil 300, for transmitting electromagnetic flux to intercept circumferentially-oriented degradation (not shown) in tube 70. Circumferential coil 300 may be generally semi-annular in transverse cross section and has a longitudinal axis oriented generally parallel with respect to the longitudinal axis of tube 70. Connected to each coil 290/300 and centrally disposed in a recess 310 defined by each semi-annular coil 290/300 is a generally cylindrical receiving core or coil 320, which may be ferrite, for receiving or sensing the electromagnetic eddy currents generated in sleeve 120 and tube 70.

Referring yet again to FIGS. 3, 4, 5, 6, 7, 8 and 9, connected to a proximal end portion 140 of support body 200 is a flexible conduit 330, for reasons disclosed hereinbelow. Engaging conduit 330 and therefore connected to support body 200, is rotation means, such as a rotator 340, for rotating conduit 330 about its longitudinal axis. It will be appreciated that as conduit 330 rotates about its longitudinal axis, support body 200, which is connected thereto, also rotates about its longitudinal axis to a like extent. Rotator 340 is therefore capable of simultaneously rotating bladder 240, sensors 250/260 and sleeve 120 relative to inner diameter 71 of tube 70 as rotator 340 rotates conduit 330 which is connected to support body 200. It will be appreciated from the description immediately hereinabove, that sleeve 120 is stationary relative to sensors 250/260 as rotator 340 rotates support body 200 because sleeve 120 is secured to support body 200 by means of inflated bladder 240. In this manner, the material properties of sleeve 120 through which the electromagnetic energy is transmitted and received are radially invariant relative to sensors 250/260.

Referring again to FIGS. 3, 4, 5, 6, 7, 8 and 9, engaging conduit 330, and therefore connected to support body 200, is translation means, such as pusher/puller mechanism 350, for translating (i.e., pushing and pulling) support body 200. That is, pusher/puller mechanism 350 simultaneously translates support body 200, sensors 250/260, bladder 240 and sleeve 120 relative to inner diameter 71 of tube 70 as pusher/puller mechanism 350 translates support body 200. It will be appreciated from the description immediately hereinabove, that sleeve 120 is stationary relative to sensors 250/260 as pusher/puller mechanism 350 translates support body 200 because sleeve 120 is secured to support body 200 by means of inflated bladder 240. In this manner, the material properties of sleeve 120 through which the electromagnetic energy is transmitted and received are axially invariant relative to sensors 250/260. Rotator 340 and pusher/puller mechanism 350 may be of the type such as is disclosed, for example, in commonly owned U.S. Pat. No. 4,901,578 titled "Probe Carrier Drive Assembly" issued Feb. 20, 1990 in the name of Bernard A. Brill, III, the disclosure of which is hereby incorporated by reference.

Referring again to FIGS. 3, 4, 5, 6, 7, 8 and 9, in fluid communication with bladder 240 is a flexible fluid supply conduit 360, for reasons disclosed hereinbelow. In fluid communication with one end of conduit 360 is fluid supply means, such as a fluid reservoir 370, for supplying fluid (e.g., water or air) to bladder 240 in order to pressurize bladder 240 so that bladder 240 radially expands to intimately engage inside diameter 130 of sleeve 120. The other end of conduit 360 is in communication with channel 220 formed in support body 200. Conduit 360 extends through conduit 330. A solenoid valve 380 may be in fluid communication with and integrally connected to conduit 360 for suitably controlling the flow of the fluid to channel 220 and for withdrawing the fluid from channel 220. It will be appreciated from the disclosure hereinabove that as fluid is supplied to channel 220, bladder 240 radially expands to engage inside diameter 130 and as fluid is withdrawn from channel 220, bladder 240 radially contracts to disengage inside diameter 130.

Referring again to FIGS. 3, 4, 5, 6, 7, 8 and 9, electrically connected to sensors 250/260, such as by electrically conducting wires 385, is activator/recorder means, such as an activator/recorder 390, for recording the presence of degradation sensed by sensors 250/260. Wires 385 extend through conduit 330 and through a passageway 387 formed in support body 200. In the preferred embodiment of the invention, activator/recorder 390 includes a Cathode Ray Tube (CRT) monitor for displaying images of the degradation sensed by sensors 250/260. Activator/recorder 390 may also include a paper strip chart 395 for permanently recording the images of the degradation sensed by sensors 250/260. Moreover, as disclosed hereinabove, activator/recorder 390 includes means for activation and operating sensors 250/260 so that sensors 250/260 suitably transmit electromagnetic energy and then detect the resulting eddy currents generated in sleeve 120 and tube 70.

Figure 3:
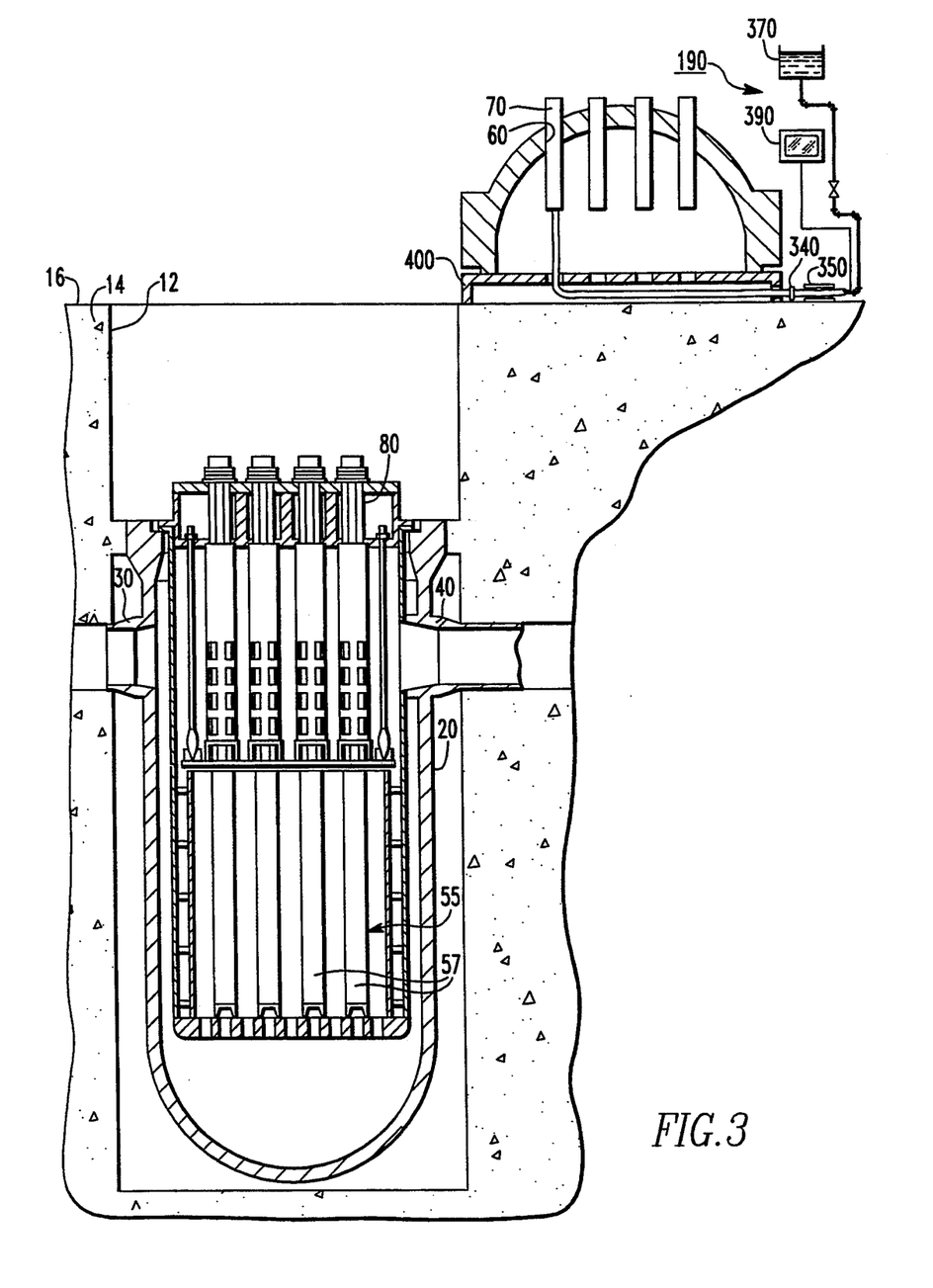
FIG. 3 shows in partial vertical section, the pressure vessel having the closure removed therefrom and mounted on a platform for inspecting the penetration tube.
Figure 4:
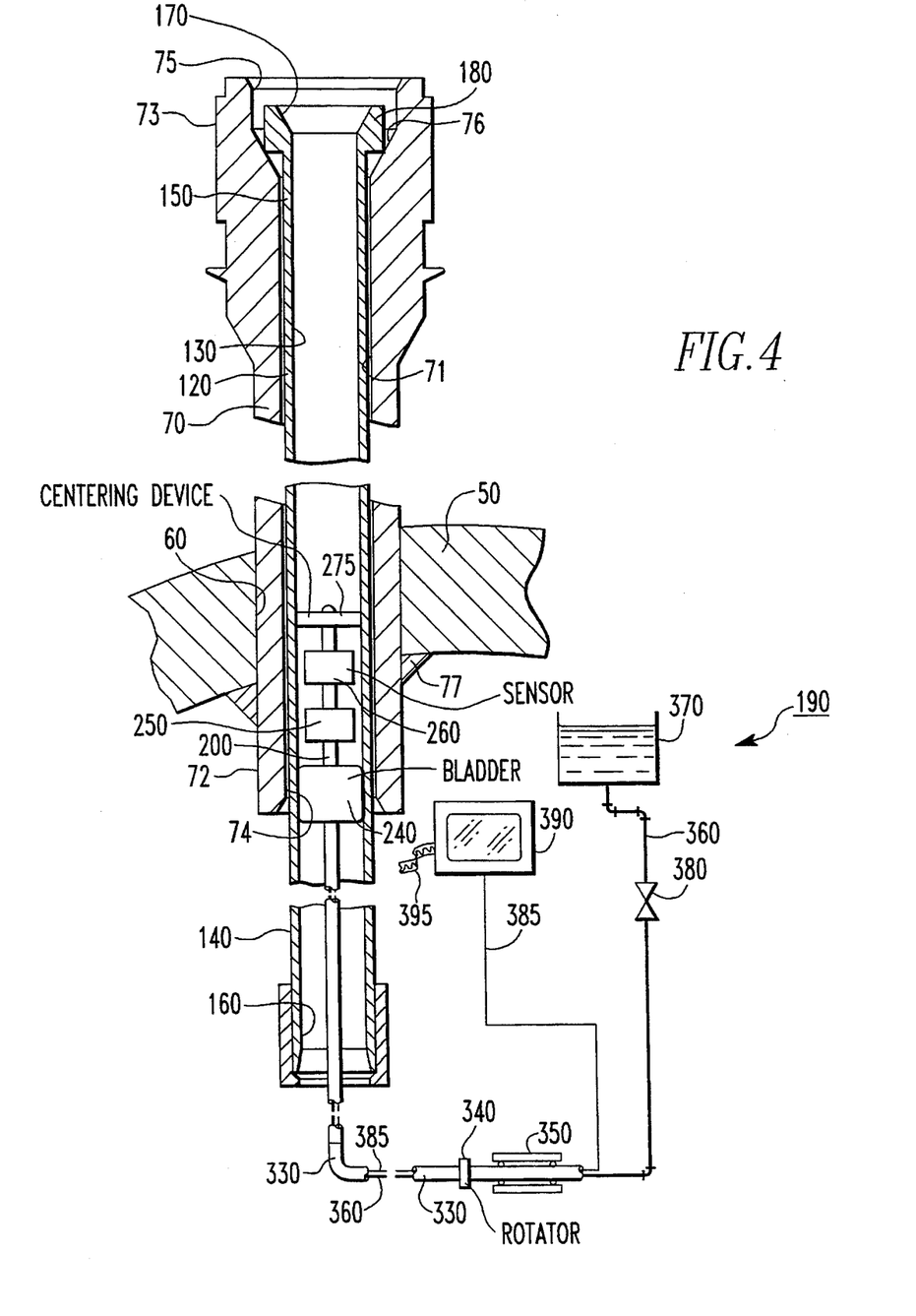
FIG. 4 shows in elevation the invention in operative condition to inspect the tube.
Figure 5:
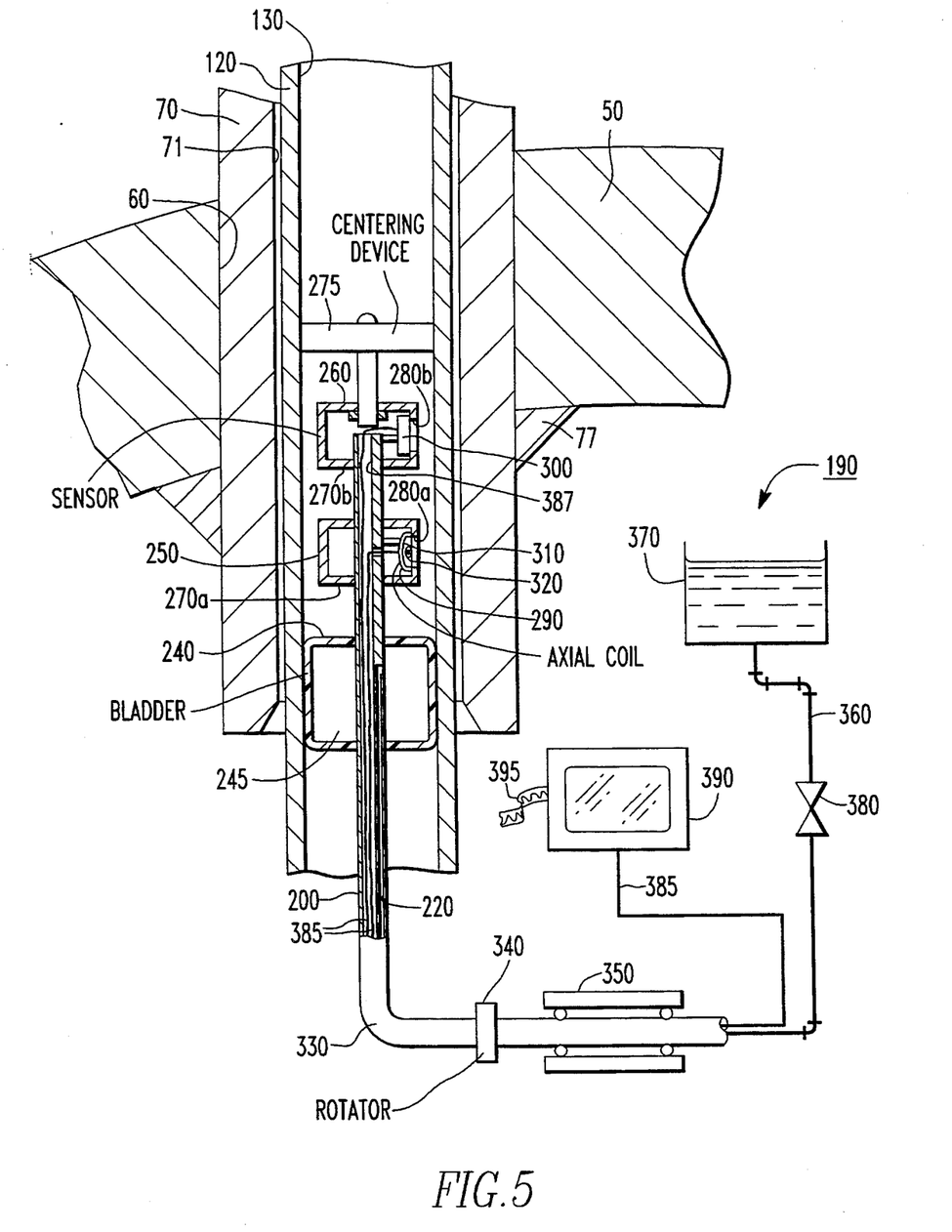
FIG. 5 shows in partial elevation the invention in operative condition to inspect the tube.
Figure 6:
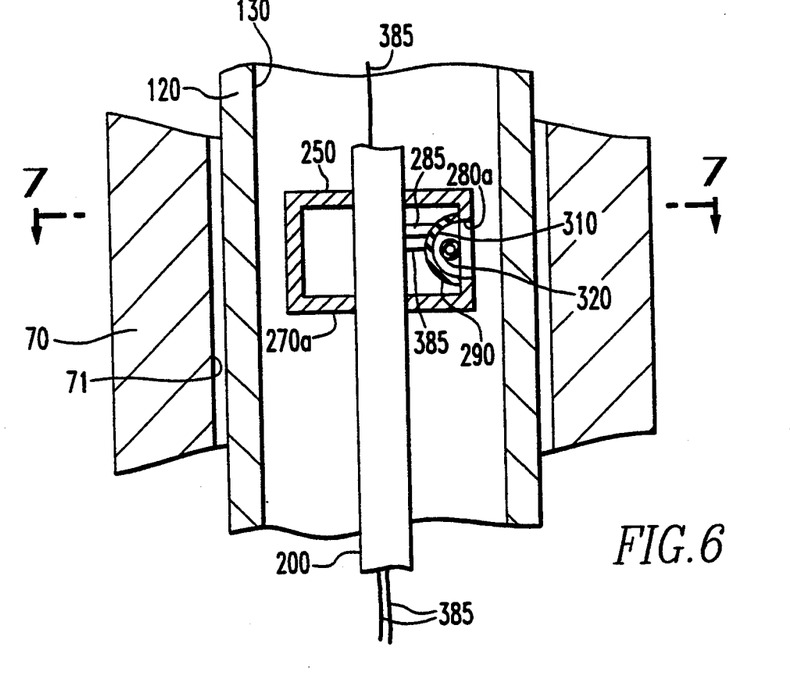
FIG. 6 shows in partial elevation a first sensor to inspect the tube for axially-oriented degradation.
Figure 7:
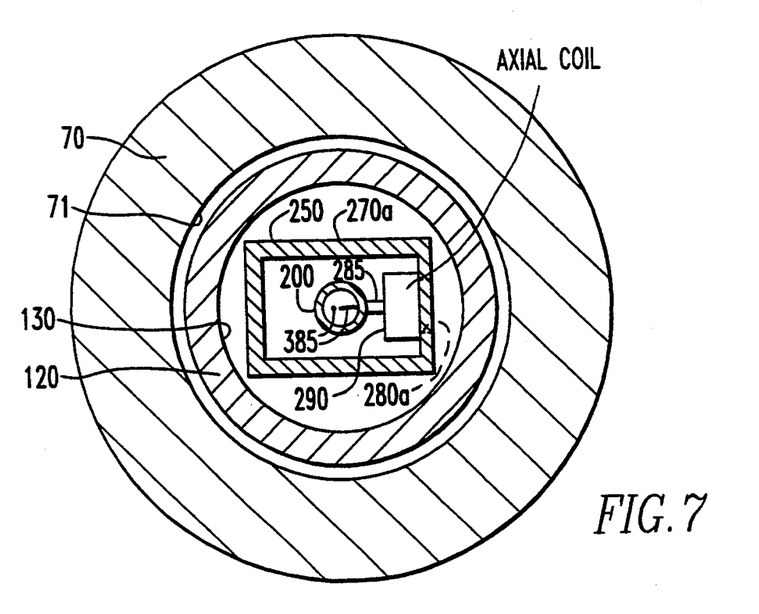
FIG. 7 is a view in horizontal section of the first sensor taken along section line 7—7 of FIG. 6.
Figure 8:
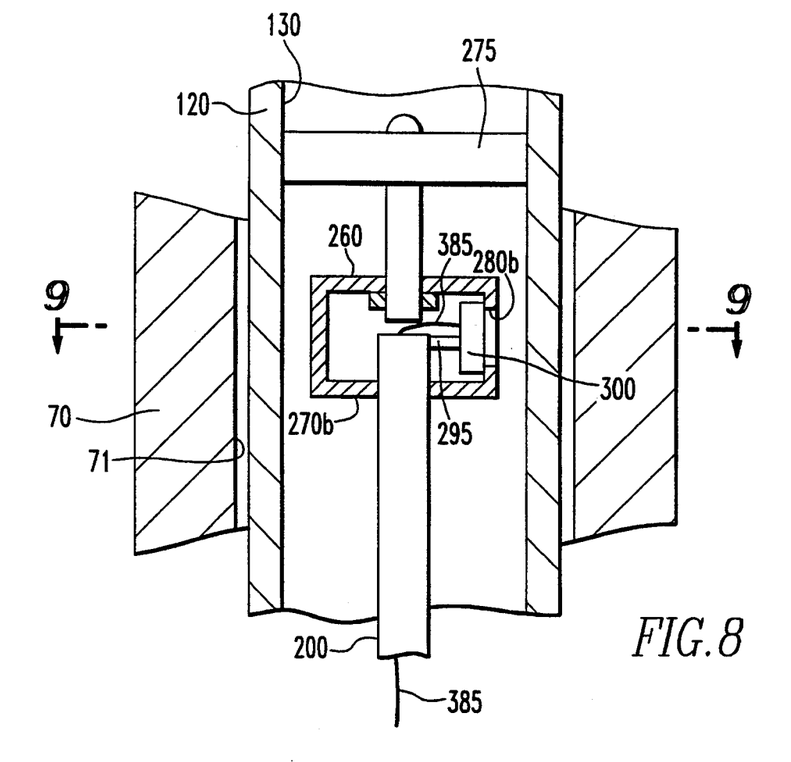
FIG. 8 shows in partial elevation a second sensor to inspect the tube for circumferentially-oriented degradation.
Figure 9:
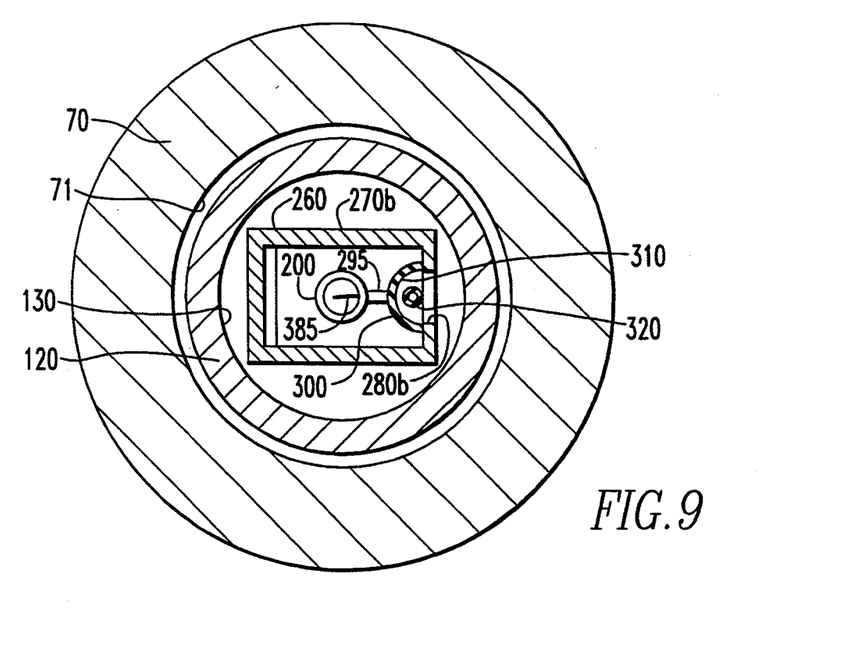
FIG. 9 is a view in horizontal section of the second sensor taken along section line 9—9 of FIG. 8.

As best seen in FIG. 3, a platform 400 is disposed on top surface 16 of containment structure 14. Closure head 50 is mounted thereon for conveniently performing the inspection of tube 70. In this regard, platform 400 has apertures 410 transversely therethrough for passage of support body 200 and its associated bladder 240, sensors 250/260 and conduit 330.

OPERATION

The CRDMs 90, coil stacks 110 and pressure housing 100 are removed from each CRDM penetration tube 70. Platform 400 is disposed on surface 16 of containment structure 14. Closure head 50 and its associated penetration tubes 70 are removed from shell 20 and disposed on platform 400. Next, apparatus 190 is disposed sufficiently near closure head 50 to perform the inspection process.

In this regard, support body 200 is remotely inserted through one of the apertures 410 of platform 400, through open mouth 160 and into inside diameter 130 of sleeve 120 by any suitable mans, such as by a suitable robotic device (not shown). Support body 200 is centered in inside diameter 130 by centering device 275. Pusher/puller mechanism 350 is operated to advance support body 200 along the longitudinal axis of sleeve 120. Support body 200 is advanced in sleeve 120 until one of the sensors, for example sensor 250, reaches a predetermined axial location (e.g., adjacent and parallel to weldment 77) in sleeve 120. Operation of pusher/puller mechanism 350 is then stopped and valve 380 is operated to supply fluid from reservoir 370, to channel 200, and thence through opening 230 into variable volume 245 so as to increase the volume of variable volume 245 for expanding bladder 240 into intimate engagement with inside diameter or wall 130. As bladder 230 engages inside wall 130, it secures support body 200 to inside wall 130. Rotator 340 is operated to rotate conduit 330 and thus support body 200 through an angle of slightly greater than 360 degrees. As support body 200 rotates, sensors 250/260 rotate to a like extent for radially scanning sleeve 120 and tube 70. In order to accomplish the scanning, activator/recorder 390 is operated to cause axial coil 290 of sensor 250 (and/or circumferential coil 300 of sensor 260) to radially transmit electromagnetic energy radially outwardly such that the electromagnetic energy propagates through sleeve 120 and tube 70. Activator/recorder 390 is also operated to cause receiving coil 320 to sense the eddy currents generated in sleeve 120 and tube 70. As activator/recorder 390 and sensors 250/260 are operated, images of the degradation are displayed on the CRT monitor belonging to activator/recorder 390. In addition, paper strip chart 395 may be printed by activator/recorder 390 to record the degradation for later viewing, if desired.

After sensor 250 (and sensor 260) completes it greater than 360 degree rotation, rotator 340 is stopped and pusher/puller mechanism 350 is again operated to axially increment support body 200, and thus sensor 250 (and also sensor 260) connected thereto, to another axial position in sleeve 120. Rotator 340 is again operated in the manner described hereinabove to radially scan another portion of tube 70. After the desired scanning of tube 70 is completed, valve 380 is operated to withdraw the fluid from bladder 240 to depressurize bladder 240 and disengage bladder 240 from inside diameter 130. After bladder 240 disengages inside diameter 130, it is removed from sleeve 120 in substantially the reverse order of its insertion into sleeve 120.

It will be understood from the immediately foregoing description that sensors 250/260 radially scan a first portion of tube 70 by being moved by rotator 340, and are then axially incremented by being moved by pusher/puller mechanism 350. At this point, sensors 250/260 are in position to radially scan a second portion of tube 70. Alternatively, sensors 250/260 may be moved to axially scan a longitudinal first portion of tube 70 by being moved by pusher/puller mechanism 350, and then radially incremented by being moved by rotator 340. At this point, sensors 250/260 are in position to axially scan a second portion of tube 70. In addition, rotator 340 and pusher/puller mechanism 350 may be simultaneously operated to helically scan tube 70. Helical movement of the sensors accomplishes the required scanning in less time. Moreover, sensors 250/260 need not be eddy current sensors; rather, sensors 250/260 may be ultrasonic sensors for radially transmitting sonic energy (i.e., sound waves) that penetrate sleeve 120 and tube 70 and for receiving sonic energy reflected therefrom. When ultrasonic sensors are used, a suitable couplant (e.g., demineralized water) is interposed between sleeve 120 and tube 70 to efficiently conduct the sound waves therethrough. It will be further understood that sensors 250/260 are capable of scanning weldments 77 for degradation in substantially the same manner it is used to scan tube 70 for degradation.

By way of example only, and not by way of limitation, CRDM penetration tube 70, which may be "INCONEL ALLOY 600" may have an outside diameter of approximately 102 mm to fit within opening 60 and an inner diameter 71 of approximately 70 mm. The penetration tube 70 also may have a length of approximately 900 mm. Sleeve 120, which may be "TYPE 304" stainless steel, may have an outside diameter of approximately 63.5 mm to fit within tube 70 and an inside diameter 130 of approximately 54 mm to receive the CRDM components. The oval deviation or distortion of sleeve 120 from nominal design values may be approximately 2 mm. Activator/recorder 390 may be of the type associated with the Hocking Vector S900 low frequency eddy current system available from R. L. Holliday Company, Incorporated located in Pittsburgh, Pa. The minimum data acquisition rate of the system from R.L. Holliday Company is such as to acquire a data point at approximately each one degree (approximately 0.5 mm of the circumference of tube 70) of rotation of sensors 250/260. Such an eddy current system includes a power supply module, a frequency generator module, a channel module, and an amplifier module. Such an eddy current system is capable of operating at frequency settings of 1, 3, 10, 30, 100, 300, and 1000 kHz so that the optimum performance settings of sensors 250/260 can be selected. Applicants have discovered that sensor operation at approximately one to 10 kHz provides optimum results for sensing degradation in tube 70. As contemplated herein, this eddy current system measures the sensor transmission signal at approximately 10 volts peak-to-peak in the sensor transmission/sensing mode. The sensor signals are displayed by this system as Lissajous (i.e., pseudo-impedance plane) time-history data on the monitor and/or strip chart 395 belonging to activator/recorder 390. Alternatively, the data may be displayed as Z-theta "X-scan" style data maps on the monitor and/or strip chart 395.

Again, by way of example only, and not by way of limitation, each sensor 250/260 may comprise a uniform field eddy current coil for transmitting electromagnetic energy and a ferrite-cored coil for sensing the eddy currents produced by the transmitted electromagnetic energy. The transmission coil may be machined from a torroidal core with coils wound to provide a measured approximate 100 ohm. resistance at approximately 1 kHz. The sensing coil may be a ferrite core machined from a ferrite rod with coils wound to provide a measured approximately 100 ohm resistance at approximately 2.45 kHz.

It will be evident from the teachings herein that an advantage of the present invention is that the material properties of sleeve 120 are invariant relative to the sensors 250/260 as support body 200, sensors 250/260, bladder 240 and sleeve 120 are rotated and translated because sleeve 120 is stationary with respect to sensors 250/260 due to sleeve 120 being secured to support body 120 by bladder 240. Thus, the material properties of sleeve 120 through which the electromagnetic energy is transmitted and received are invariant relative to sensors 250/260. In this manner, the eddy current signals received by sensors 250/260 are not masked by undesirably varying interference due to the nonhomogeneity of sleeve 120.

Although the invention is fully illustrated and described herein, it is not intended that the invention as illustrated and described be limited to the details shown, because various modifications may be obtained with respect to the invention without departing from the spirit of the invention or the scope of equivalents thereof. For example, the securing means need not be the bladder 240; rather, the securing means may be radially outwardly movable fingers adapted to engage inside diameter 130 of sleeve 120 for securing support body 200 to inside diameter 130 during the inspection process. As another example, sleeve 120 may have a hole cut through the wall thereof, the hole being located opposite either sensor 250 or 260, or both sensors 250 and 260, so that the inspection signal transmitted and sensed by the sensors do not pass through the material comprising sleeve 120.

Therefore, what is provided is an apparatus and method for inspecting a tubular member for degradation, which tubular member may be a control rod drive mechanism penetration tube of the kind typically found in nuclear power reactor pressure vessels.

What is claimed is:

1. An apparatus for inspecting a tubular member for degradation, the tubular member surrounding a rotatable sleeve, comprising:
   (a) a support body adapted to be disposed in the sleeve;
   (b) securing means connected to said support body and adapted to engage the sleeve for securing said support body to the sleeve;
   (c) sensor means connected to said support body for sensing the degradation in the tubular member; and
   (d) rotation means connected to said support body for rotating said support body, whereby said support body, said securing means, said sensor means and the sleeve simultaneously rotate in the tubular member as said rotation means rotates said support body.

2. The apparatus of claim 1, wherein said sensor means is an eddy current sensor.

3. The apparatus of claim 1, wherein said sensor means is an ultrasonic sensor.

4. An apparatus for inspecting a tube for degradation, the tube having an inner surface surrounding a sleeve rotatably and translatably disposed in the tube, the sleeve having an inside surface and nonuniform material properties, comprising:
   (a) a support body sized to be disposed within the sleeve;
   (b) an expandable bladder surrounding said support body and connected thereto to intimately engage the inside surface of the sleeve for securing said support body to the inside surface of the sleeve;
   (c) a sensor connected to said support body for sensing the degradation in the tube, said sensor adapted to transmit energy through the sleeve and into the tube and adapted to sense energy perturbations in the sleeve and the tube; and
   (d) a rotator connected to said support body for rotating said support body, whereby said support body, said bladder, said sensor and the sleeve simultaneously rotate within the tube as said rotator rotates said support body so that said sensor radially senses the tube for degradation and whereby the sleeve is stationary relative to said sensor as said rotator rotates said support body so that the material properties of the sleeve are radially invariant relative to said sensor.

5. The apparatus of claim 4, further comprising a pusher/puller mechanism connected to said support body for translating said support body relative to the inner surface of the tube, whereby said support body, said sensor, said bladder and the sleeve simultaneously translate within the tube as said pusher/puller mechanism translates said support body so that said sensor axially senses the tube for degradation and whereby the sleeve is stationary relative to said sensor as said pusher/puller mechanism translates said support body so that the material properties of the sleeve are axially invariant relative to said sensor.

6. The apparatus of claim 4, further comprising a fluid reservoir in communication with said bladder for supplying a fluid to said bladder for expanding said bladder into intimate engagement with the inside surface of the sleeve.

7. The apparatus of claim 4, further comprising an activator/recorder connected to said sensor for activating said sensor and for recording the degradation sensed by said sensor.

8. The apparatus of claim 4, wherein said sensor is an eddy current sensor for transmitting and sensing electromagnetic energy.

9. The apparatus of claim 4, wherein said sensor is an ultrasonic sensor for transmitting and sensing sonic energy.

10. In a reactor pressure vessel closure head, an apparatus for nondestructively inspecting a reactor pressure vessel penetration tube for degradation, the tube having an inner surface surrounding a freely rotatable and translatable sleeve concentrically mounted in the tube, the sleeve having an inside surface and nonuniform material properties, the apparatus comprising:
(a) an elongate support body having a longitudinal axis and sized to be disposed within the sleeve, said support body having an exterior surface thereon and a channel inside said support body which terminates in an opening on the exterior surface of said support body;
(b) a radially expandable bladder surrounding a portion of said support body and connected thereto to intimately engage the inside surface of the sleeve for securing said support body to the inside surface, said bladder covering the opening;
(c) a sensor connected to said support body for sensing the degradation in the tube, said sensor adapted to transmit energy through the sleeve and into the tube and adapted to sense energy perturbations in the sleeve and the tube, said sensor adapted to generate an electrical signal in response to the energy perturbations sensed thereby;
(d) a rotator connected to said support body for rotating said support body about the longitudinal axis of the support body, whereby said support body, said bladder, said sensor and the sleeve simultaneously rotate in the tube as said rotator rotates said support body, so that said sensor radially senses the tube for degradation and whereby the sleeve is stationary relative to said sensor as said rotator rotates said support body so that the material properties of the sleeve through which the energy is transmitted are radially invariant relative to said sensor; and (e) a pusher/puller mechanism connected to said support body for translating said support body in the tube, whereby said support body, said sensor, said bladder and the sleeve simultaneously translate in the tube as said pusher/puller mechanism translates said support body so that said sensor axially scans the tube for degradation and whereby the sleeve is stationary relative to said sensor as said pusher/puller mechanism translates said support body so that the material properties of the sleeve through which the energy is transmitted are axially invariant relative to said sensor.

11. The apparatus of claim 10, further comprising a fluid reservoir in fluid communication with the channel in said support body for supplying a fluid to the channel, through the opening and to the bladder for pressurizing said bladder so that said bladder radially expands to intimately engage the inside surface of the sleeve.

12. The apparatus of claim 10, further comprising an activator/recorder electrically connected to said sensor for activating said sensor and for recording the signal generated by said sensor.

13. The apparatus of claim 10, wherein said sensor is an eddy current sensor for transmitting electromagnetic energy and for sensing electromagnetic eddy currents produced thereby in the sleeve and the tube.

14. The apparatus of claim 10, wherein said sensor is an ultrasonic sensor for transmitting sonic energy and for sensing sound waves reflected from the sleeve and the tube.

15. In a nuclear system, an apparatus for inspecting a tubular member of the nuclear system for degradation, the tubular member surrounding a movable sleeve, comprising:
(a) a sensor for sensing the degradation of the tubular member over an incremental portion of the tubular member at a given point in time, the sensor being sized to be inserted within the sleeve;
(b) means for maintaining the sensor in fixed relation to the sleeve, so that the sensor always focuses on the same portion of the sleeve when in a sensing mode as the sleeve is moved; and
(c) means for moving the sensor and the sleeve within the tubular member over the incremental portion of the tubular member to be inspected.

16. A method of inspecting a tubular member for degradation, the tubular member surrounding a rotatable sleeve, comprising the steps of:
(a) disposing a support body in the sleeve, the support body having a bladder and a sensor connected thereto;
(b) securing the support body to the sleeve by engaging the bladder with the sleeve;
(c) operating the sensor for sensing the degradation in the tubular member;
(d) rotating the support body by operating a rotator connected thereto, whereby the support body, the bladder, the sensor and the sleeve simultaneously rotate in the tubular member as the rotator rotates the support body.

17. The method of claim 16, wherein said step of operating the sensor comprises the step of operating an eddy current sensor.

18. The method of claim 16, wherein said step of operating the sensor comprises the step of operating an ultrasonic sensor.

19. A method of inspecting a tube for degradation, the tube having an inner surface surrounding a rotatable and translatable sleeve, the sleeve having an inside surface and nonuniform material properties, comprising the steps of:
- (a) disposing a support body within the sleeve, the support body having an expandable bladder surrounding the support body and connected thereto, the support body having a sensor connected thereto;
- (b) securing the support body to the inside surface of the sleeve by expanding the bladder into intimate engagement with the inside surface of the sleeve;
- (c) operating the sensor to transmit energy through the sleeve and into the tube and to sense energy perturbations in the sleeve and the tube for sensing degradation in the tube; and
- (d) rotating the support body by operating a rotator connected to the support body, whereby the support body, the bladder, the sensor and the sleeve simultaneously rotate within the tube as the rotator rotates the support body, so that the sensor radially scans the tube for degradation and whereby the sleeve is stationary relative to the sensor as the rotator rotates the support body so that the material properties of the sleeve are radially invariant relative to the sensor.

20. The method of claim 19, further comprising the step of translating the support body relative to the inner surface of the tube by operating a pusher/puller mechanism connected to said support body, whereby the support body, the bladder, the sensor and the sleeve simultaneously translate within the tube as the pusher/puller mechanism translates the support body so that the sensor axially senses the tube for degradation and whereby the sleeve is stationary relative to the sensor as the pusher/puller mechanism translates the support body so that the material properties of the sleeve are axially invariant relative to the sensor.

21. The method of claim 19, wherein said step of securing the support body to the inside surface of the sleeve comprises the step of supplying a fluid to the bladder for expanding the bladder.

22. The method for claim 19, further comprising said step of operating an activator/recorder electrically connected to the sensor for activating the sensor and for recording the degradation sensed by the sensor.

23. The method of claim 19, wherein said step of operating the sensor comprises the step of operating an eddy current sensor for transmitting and sensing electromagnetic energy.

24. The method of claim 19, wherein said step of operating the sensor comprises the step of operating an ultrasonic sensor for transmitting and sensing sonic energy.

25. In a reactor pressure vessel closure head, a method of nondestructively inspecting a reactor pressure vessel penetration tube for degradation, the tube having an inner surface surrounding a rotatable and translatable sleeve concentrically mounted in the tube, the sleeve having an inside surface and nonuniform material properties, the method comprising the steps of:
- (a) disposing an elongate support body within the inner surface of the tube, the support body having a longitudinal axis, the support body having an exterior surface thereon and a channel inside the support body which terminates in an opening on the exterior surface of the support body, the support body having a radially expandable bladder surrounding a portion of the support body and connected thereto, the support body having a sensor connected thereto to sense the tube for degradation, the sensor adapted to transmit energy through the sleeve and into the tube and adapted to sense energy perturbations in the sleeve and the tube, the sensor adapted to generate an electrical signal in response to the energy perturbations sensed thereby;
- (b) securing the support body within the sleeve by radially expanding the bladder into intimate engagement with the inside surface of the sleeve, said step of securing the support body to the inside surface of the sleeve including the step of supplying a fluid to the bladder for expanding the bladder by releasing the fluid from a fluid reservoir connected to the bladder;
- (c) operating the sensor to transmit energy through the sleeve and into the tube and to sense energy perturbations in the sleeve and the tube for sensing the degradation in the tube, the sensor capable of generating an electrical signal in response to the energy perturbations sensed thereby;
- (d) rotating the support body about the longitudinal axis of the support body by operating a rotator connected to the support body, whereby the support body, the bladder, the sensor and the sleeve simultaneously rotate within the tube as the rotator rotates the support body, so that the sensor radially senses the tube for degradation and whereby the sleeve is stationary relative to the sensor as the rotator rotates the support body so that the material properties of the sleeve through which the energy is transmitted are radially invariant relative to the sensor; and
- (e) translating the support body in the tube by operating a pusher/puller mechanism connected to the support body, whereby the support body, the bladder, the sensor and the sleeve simultaneously translate within the tube as the pusher/puller mechanism translates the support body, so that the sensor axially senses the tube for degradation and whereby the sleeve is stationary relative to the sensor as the pusher/puller mechanism translates the support body so that the material properties of the sleeve through which the energy is transmitted are axially invariant relative to the sensor.

26. The method of claim 25, further comprising the step of simultaneously rotating and translating the support body to helically sense the tube for degradation by simultaneously operating the rotator and the pusher/puller mechanism.

27. The method of claim 25, further comprising the step of operating an activator/recorder electrically connected to the sensor for activating the sensor and for recording the signal generated by the sensor.

28. The method of claim 25, wherein the step of operating the sensor comprises the step of operating an eddy current sensor for transmitting electromagnetic energy and for sensing electromagnetic eddy currents produced thereby in the sleeve and the tube.

29. The method of claim 25, wherein the step of operating the sensor comprises the step of operating an ultrasonic sensor for transmitting sonic energy and for sensing sound waves reflected from the sleeve and the tube.

* * * * *